United States Patent [19]

Mitteldorf et al.

[11] 4,346,299
[45] Aug. 24, 1982

[54] CELL FOR CONTAINING FLUID TO BE ANALYZED BY X-RAY SPECTROSCOPY

[75] Inventors: Arthur J. Mitteldorf, Scotch Plains; Joseph Marcovecchio, Berkeley Heights; Rodolfo A. Boquiron, New Monmouth, all of N.J.

[73] Assignee: Spex Industries Inc., Metuchen, N.J.

[21] Appl. No.: 264,566

[22] Filed: May 18, 1981

[51] Int. Cl.³ .............................................. G01N 21/00
[52] U.S. Cl. .................................. 378/204; 422/102; 220/319; 220/269; 206/628
[58] Field of Search ........................... 206/524.1, 628; 220/DIG. 6, DIG. 27, 368, 369, 271, 269; 422/102; 250/456; 356/246

[56] References Cited

U.S. PATENT DOCUMENTS

| | | | |
|---|---|---|---|
| 2,177,359 | 10/1939 | Baker | 220/319 X |
| 3,135,451 | 6/1964 | Bauder et al. | 206/628 |
| 3,270,871 | 9/1966 | Pushkin | 220/319 |
| 3,407,957 | 10/1968 | Robinson | 206/628 |
| 3,647,386 | 3/1972 | Gilford | 229/56 |
| 3,963,933 | 6/1976 | Henkes, Jr. | 250/456 |
| 4,253,582 | 3/1981 | Shields | 220/269 |
| 4,264,204 | 4/1981 | McCormick | 356/246 |

Primary Examiner—Joseph Man-Fu Moy
Attorney, Agent, or Firm—Robert A. Green

[57] ABSTRACT

The disclosure is of a fluid analyzing cell including a cylinder having an open end closed by a plastic film and a closed end wall including means therein for easily rupturing said closed end wall to accommodate fluid expansion or venting of gases within the cell.

4 Claims, 2 Drawing Figures

CELL FOR CONTAINING FLUID TO BE ANALYZED BY X-RAY SPECTROSCOPY

BACKGROUND OF THE INVENTION

X-ray spectrochemical analysis is a technique for measuring, both qualitatively and quantitatively, the elemental composition of a substance. In liquid, solid or gaseous form, a continuous spectrum of x-radiation is directed to the surface of the sample which then emits x-rays characteristic of its elemental makeup. The wavelengths or energy pattern emitted, distinct for each element, form the basis for qualitative analysis; their intensity forms the basis for quantitative analysis.

The reliability of quantitative determinations depends on the physical and chemical uniformity of each of the samples and the reference standards. Thus, if a sample is a liquid, its viscosity, temperature, chemical composition, surface, and other physical and chemical parameters must be kept as close to that of the standards to achieve the base accuracy and precision of measurement.

Liquids present a special analytical problem. From long experience, it has been found that the best accuracy and precision are attained when the liquid is analyzed with so-called inverted optics. That is, the x-ray beam is directed upwards against the sample which is contained in a cell or container fitted with a thin window, generally a plastic film, that is virtually transparent to x-rays. For many years, cells for carrying liquids to be analyzed have been commercially available, and these cells are generally inexpensive and are molded from a polymer with a plastic film window stretched into place by a plastic or elastomer ring.

Such cells exhibit limitations especially when, to improve accuracy or lower the limit of detection, the sample is exposed to x-rays for an extended period of time, perhaps several minutes. Under such circumstances, the liquid, absorbing much of the x-rays, heats up and thereby expands in volume. The thin plastic film window then "balloons" and, if heated still further, may actually burst or permit leakage at the seal. In addition, even a small departure from flatness of the plastic film window causes a change in the intensity of x-rays which, in turn, degrades the accuracy of the analysis. To prevent this, it has been a common practice to pierce the floor of the cell, (the top of the cell when it is in the x-ray spectrometer), to permit venting. In some commercial cells, a small portion of the floor is made thinner to facilitate piercing.

At the current state of the art, a tool such as a needle is used by the operator to pierce the floor of the cell to provide the desired venting. It can be seen that a needle, which is separate from the x-ray apparatus itself, may be troublesome to handle, and, in addition, such a needle might be dropped and lost, or other unexpected problems might arise. Also, if the liquid under test has been heated and expanded beyond a critical amount, it may flow over the edge of the floor of the cell, and, depending on the liquid, the x-ray apparatus may be fouled or damaged. Presently available cells are all subject to these problems.

DESCRIPTION OF THE INVENTION

Figure 1:
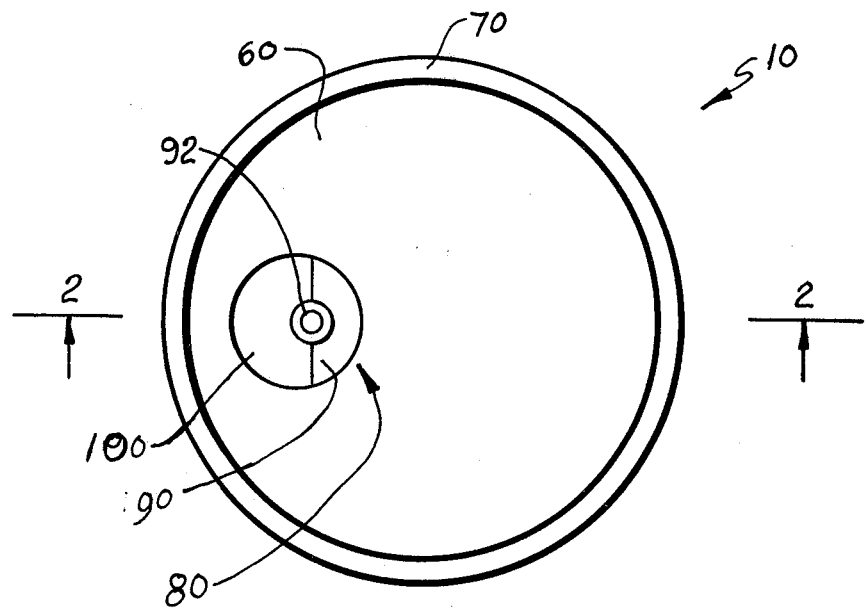
FIG. 1 is a plan view of a cell embodying the invention.
Figure 2:
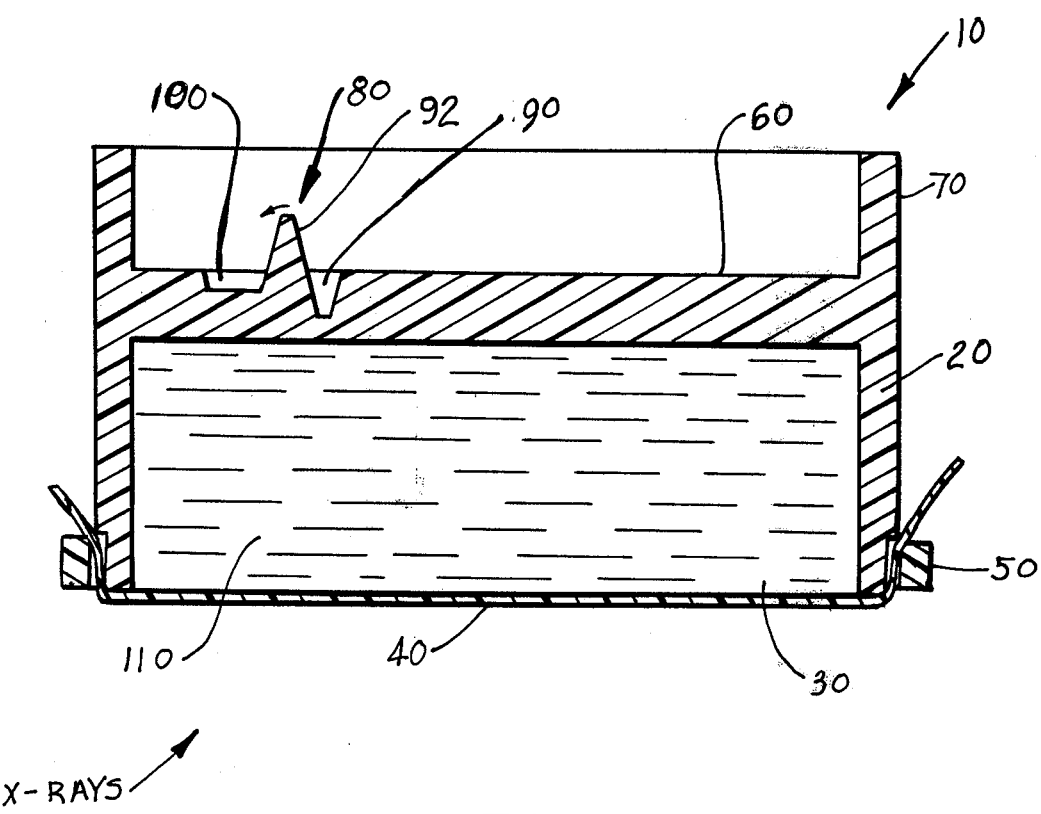
FIG. 2 is a sectional view along the lines 2—2 in FIG. 1.

The apparatus of the invention 10 is known as a cell and comprises a cylinder 20 of a synthetic resinous material having an open lower end 30, across which a film 40 of synthetic resinous material such as Mylar is stretched and secured in place by a ring 50 slipped over the open end of the cylinder and seated on an annular notch in the side wall of the cylinder. The upper end of the cylinder 20 is closed by an integral wall 60 which includes an upstanding peripheral rim 70 which extends above wall 60, for a purpose to be described. In addition, the end wall 60 includes integral means 80 for puncturing the wall 60.

The puncturing means 80 is disposed off-center near the upstanding rim 70 and includes a vertical pin or post 92 which is off-center on a generally circular structure which defines the puncturing means 80. The means 80 includes a semi-circular portion 90 of minimal thickness, which provides an area of weakness in the wall 60, and a semi-circular portion 100 of somewhat greater thickness, both such thicknesses being less than the thickness of the end wall 60 itself.

In operation of the invention, the open-ended cylinder 20 is held open-end up and filled with a fluid 110, such as oil, to be analyzed by x-ray spectroscopy, and the plastic film 40 and ring 50 are set in place. The cell thus formed is then inserted in the x-ray apparatus with the end wall 60 up and film 40 down. Before the test is performed, during which the fluid under test heats and expands, the operator pivots the pin 92 in the direction of the thick wall 100, and this causes the thin wall 90 to rupture and permit the fluid in the cell to expand. According to the invention, any fluid which escapes is contained by the upstanding peripheral wall 70 and cannot overflow and damage the x-ray apparatus. The test is now run properly and without distortion of film 40.

It can be seen that the apparatus of the invention includes integral, effective means for puncturing the cell to permit expanded fluid to escape. It also includes means for preventing the escaped fluid from overflowing and damaging any associated apparatus.

What is claimed is:

1. A fluid cell for x-ray analysis comprising
    a cylinder having a first closed end defined by a wall and a second open end,
    a thin sheet of synthetic resinous material fitted over said open end and adapted to pass radiation through it into a quantity of fluid disposed in said cylinder, with said cylinder disposed so that said second end is facing down and said first end is up,
    wall-rupturing means formed in said closed end for rupturing said closed end to accommodate fluid flow from within said cylinder when said fluid heats and expands due to said radiation,
    said means being formed near to but inwardly of the periphery of said wall and comprising a vertical post which rises from a portion of said wall which defines said first closed end of said cylinder, at least a part of said portion of said wall being thinner than said wall and rupturable by means of pressure applied to said post to cause said post to tend to pivot, and
    an upstanding rim rising from said wall and defining the periphery of said closed end and being of sufficient height to contain fluid which may be present on said closed end after said means has been operated to rupture said wall.

2. The cell defined in claim 1 wherein, in said wall-rupturing means, the portion of said wall surrounding the base of said post includes a first generally semi-circular portion which is thinner than said wall and a second generally semicircular portion which is thinner than said first portion whereby preferential rupturing of said second portion is achieved.

3. The cell defined in claim 1 wherein said wall-rupturing means includes a circular region in said wall, more than half of which is of a first thickness which is less than the thickness of the wall and the remainder of which is of a second thickness which is less than the first thickness.

4. The cell defined in claim 3 wherein said post rises from approximately the juncture of the two portions of different thicknesses and is thus offset from the center of said circular region.

* * * * *